(12) United States Patent
Ullrich et al.

(10) Patent No.: US 6,717,164 B2
(45) Date of Patent: Apr. 6, 2004

(54) TANNING MODULE WITH A HOUSING

(75) Inventors: Bernd Ullrich, Erlensee (DE); Ullrich Berger, Biebergemünd (DE); Ernst Smolka, Goldbach (DE); Jörn Jahnke, Hanau (DE); Stefan Greif, Fulda (DE)

(73) Assignee: Heraeus Noblelight GmbH, Hanau (DE)

( * ) Notice: Subject to any disclaimer, the term of this patent is extended or adjusted under 35 U.S.C. 154(b) by 0 days.

(21) Appl. No.: 09/988,807

(22) Filed: Nov. 20, 2001

(65) Prior Publication Data

US 2003/0075693 A1 Apr. 24, 2003

(30) Foreign Application Priority Data

Oct. 24, 2001 (DE) ..................... 201 17 223 U (51) Int. Cl.⁷ ................................. G21G 5/00
(52) U.S. Cl. .............. 250/534 R; 607/80; 607/88; 607/90; 607/91; 250/493.1
(58) Field of Search .................. 607/88, 90, 91; 250/504 R (56) References Cited

U.S. PATENT DOCUMENTS

| 4,560,883 A | * | 12/1985 | Kerschgens ............. 250/504 R |
| 4,839,513 A | * | 6/1989 | Wijtsma ..................... 607/94 |
| 4,989,343 A | * | 2/1991 | Ericsson ...................... 34/278 |
| 5,736,744 A | * | 4/1998 | Johannsen et al. ....... 250/505.1 |
| 2002/0117638 A1 | * | 8/2002 | Mewissen et al. ...... 250/504 R |

FOREIGN PATENT DOCUMENTS

| DE | 36 31 427 | 4/1976 |
| DE | 29 41 467 | 4/1981 |
| DE | 39 27 695 | 2/1991 |
| DE | 40 37 483 | 5/1992 |
| DE | 195 16 603 | 11/1996 |

* cited by examiner

Primary Examiner—John R. Lee
Assistant Examiner—Erin-Michael Gill
(74) Attorney, Agent, or Firm—Fulbright & Jaworski L.L.P.

(57) ABSTRACT

The invention relates to a tanning module with optimized guidance of the flow of cooling air, with a housing, a reflector, and at least one discoid radiation filter. The housing has the shape of a quadrilateral pyramid with a rectangular base on a first side opposite the radiation filter and a flattened pyramid apex, the rectangular base facing toward the at least one radiation filter.

85 Claims, 6 Drawing Sheets

TANNING MODULE WITH A HOUSING

DESCRIPTION OF THE INVENTION

The invention relates to a tanning module having a housing, a tridimensional reflector disposed in the housing, and at least one discoid like radiation filter, the at least one radiation filter covering the radiation-emitting area of the reflector and being disposed on a first side of the housing, at least one opening being provided in the reflector for the installation and electrical connection of a tanning radiator, and the reflector having its maximum cross section in the plane of the radiation-emitting area.

Such tanning modules are disclosed, for example, in DE 29 41 467 A1, wherein a rectangular housing including fan and flow-directing baffles are used. The rectangular housing is divided into an air intake side and a delivery side, the tanning radiator being disposed on the delivery side and being indirectly cooled. The intake of cooling air, which flows along a heat filter in the housing wall, takes place on the air intake side of the housing through a lateral wall. On the delivery side of the housing the cooling air leaves the housing through the same lateral wall as it previously entered the housing on the air intake side.

DE 195 16 603 A1 discloses a low-pressure viewing field for tanning apparatus, wherein a rectangular housing including reflector and filter pane is used. The housing is suitable for the installation of several UVC tubes. The entry of cooling air into the housing takes place through an opening between housing and filter pane, the cooling air flowing along the tubes and leaving the housing again at the back of the housing.

DE 36 31 427 C2 describes a radiation apparatus with a rectangular housing, a reflector and a filter pane. To secure the filter pane against breakage, a push switch is provided which is held in its depressed position by the filter pane, but if the filter plate breaks it comes out of this position and shuts off the radiation source.

DE 39 27 695 C2 discloses a tanning apparatus with a swivelling interference filter. An infrared filter follows the interference filter in the direction of radiation emission. Depending on the inclination of the interference filter in the radiation-emitting area the limit of the transmission spectrum is shifted toward the shorter-wavelength UV-B portion or toward the long-wavelength UV-A portion. Thus, the radiation spectrum can be adjusted to the skin type of the person being irradiated by swivelling of the filter.

DE 40 37 483 C2 describes an ultraviolet radiation apparatus with safety against breakage of a filter glass pane, wherein an electrical conductor carrying current is disposed on its perimeter. If the filter glass plate breaks the conductor is broken, and the current is thereby interrupted and the tanning radiator is shut off.

The problem is to make available a tanning module which has a housing with an optimized management of the cooling air.

The problem is solved in that the housing is configured on the second side opposite the radiation filter in the form of a quadrilateral pyramid with a rectangular base and flattened apex, and that the rectangular base faces the at least one radiation filter.

Such a housing form has the advantage that the free cross section between the outside of the reflector and the inside of the housing can be kept largely symmetrical, so that when air is drawn from the area behind the reflector a uniform flow distribution is established. The temperature of the reflector is thereby equalized. In the tanning module of the invention, additional flow guiding baffles can be dispensed with, since by means of the pyramidal shape the formation of fluidic "dead corners" is avoided. In the area of the opening in the reflector which serves for the installation and connection of a tanning radiator, air can also be drawn out of the reflector space and thus the tanning radiator can be directly cooled.

The tanning module according to the invention is appropriate for tanning radiators with an electrical power output in the range of 250 W to 1000 W. It is outstandingly useful in a great variety of tanning apparatus or medical apparatus for the irradiation of the face, the upper chest, the body area, and the leg or foot area. It is also possible to install it in ceilings, for the irradiation of floor areas from greater distances. The tanning module of the invention can basically be held in any kind of mounting so that it can radiate in all directions in a virtual sphere. Several tanning modules can be mounted side by side or one after another in order to produce a larger radiation field. Also, it is possible to operate with a separate fan for each tanning module or else to operate a plurality of tanning modules with one central fan.

It is preferred with the tanning module according to the invention that the radiation filter be aligned parallel to the radiation emitting area of the reflector. Thus the dimensions of the housing can be kept small. Advantageous in this connection is also the alignment of the base of the pyramid parallel to the at least one radiation filter.

The flattened apex of the pyramid can be formed on the one hand by a planar portion of the housing wall, which can also be aligned parallel to the base of the pyramid. On the other hand the flattened apex of the pyramid can be formed by a vaulted portion of the housing wall, and it can be given a concave or convex shape in view of the base surface of the pyramid. The choice of the geometry of the flattened apex depends mainly on the conditions at the point of use of the tanning module.

The base of the pyramid can adjoin a rectangular housing wall area, which can serve, for example, to accommodate different radiation filters.

It has proven to be worth while to make the reflector in a cupular or tub-shape, the bottom of the cupular or tub-shaped reflector can be either vaulted or plane-parallel to the at least one radiation filter.

The perimeter of the reflector parallel to the radiation emitting area can then be a circle, an ellipse, a rectangle or a polygon. Especially preferred is a reflector formed of facets, in which case the perimeter of the reflector describes a polygon with twelve sides parallel to the radiation emitting area.

In particular the use of a reflector has proven useful whose height ranges from 90 mm to 95 mm and which is especially 93.6 mm high. The dodecagon in the plane of the radiation emitting area has for this reflector a preferred maximum diameter (corner to corner) ranging from 210 mm to 230 mm, and amounts especially to 210 mm. Moreover a reflector has proven useful whose height ranges from 110 mm to 125 mm and especially 118.7 mm. In this case the dodecagon has a maximum diameter (corner to corner) ranging from 170 mm to 200 mm in the plane of the radiation emitting area and amounts especially to 184 mm.

Moreover a reflector has proven useful having a height ranging from 75 mm to 90 mm and especially a height of 83.3 mm. The dodecagon in this case has a maximum diameter (corner to corner) in the plane of the radiation emitting area ranging from 205 mm to 235 mm and amounts especially to 220 mm.

The guidance of the cooling air in the housing is optimal when the housing has at least one air exhaust opening in the area of the pyramid. In that case a flange can be mounted on the air exhaust opening. Such a flange is suitable for the attachment of an air exhaust hose through which a central or off-center exhausting of air from the housing can be performed. To establish the necessary suction power at the air exhaust opening, a reducer plate may be present to reduce the size of the air exhaust opening. This is practical, for example, whenever a plurality of tanning modules are used and they are at different distances from a central fan, i.e., one used simultaneously by all tanning modules or the air exhaust is performed in a kind of serial switching of the fan from one tanning module through at least one additional one.

The tanning module of the invention can be used very flexibly if one air exhaust opening is associated with each of three sides of the pyramid. Depending on the point of use and kind of use, one of the three air exhaust openings can be selected, for example, and the other two closed.

At least one mounting is preferably provided externally on the housing for electrical terminals or components, such components being, for example, an ignition device, a switch for filter plate protection and one grounding lug.

Between the housing and the reflector an intake plate is preferably situated, the radiation emitting area of the reflector being shifted upward or downward from the plane of the air intake plate, at least one intake opening being formed between the intake plate and the reflector, and the intake plate has an opening for the reflector, and in the vertical projection onto the at least one radiation filter, it has the size of the radiation emitting area.

With this arrangement of the reflector with respect to the intake plate, an annular intake opening is preferably formed between the intake plate and the reflector, through which cooling air can be drawn toward the outer wall of the reflector from the area between the radiation filter and the radiation emitting area of the reflector. However, a plurality of preferably annularly arranged intake openings may be formed between the intake plate and the reflector, in which case an alignment as symmetrical as possible has a beneficial effect on the uniformity of the cooling of the reflector and of the radiation filter. The temperature distribution on the radiation filter has a decisive influence on its transmission properties.

It has furthermore been found practical to use an air intake plate to fasten the reflector on all sides in the plane of the radiation emitting area to the housing, in which case the air intake plate has at least one intake opening and also a cut-out for the reflector, which has in its vertical projection onto the at least one radiation filter the size of the radiation emitting area.

If an intake plate with a rectangular perimeter is used and a reflector is also used whose perimeter parallel to the radiation emitting area describes a circle, an ellipse or a polygon, the at least one intake opening is preferably arranged in the area of at least one corner of the intake plate.

The flow of cooling air is additionally optimized when four intake openings are formed in the intake plate and each intake opening is located in a corner of the intake plate.

It has proven especially useful if the at least one intake opening is enlarged along the sides of the intake plate. Preferred here is a trapezoidal intake opening, with the long side of the trapezoid pointing toward the reflector. Also, the long side of the trapezoid and its opposite side can be curved.

It is possible to fasten the reflector to the housing only through the intake plate. In that case various spacers can be provided between the intake plate and the reflector in order, for example, to form intake openings between the intake plate and the reflector.

The at least one radiation filter is to be preferably releasable from the housing with a swivelling mechanism. In that case the swivelling mechanism is to permit the radiation filter to tilt with respect to the base of the pyramid and it is to be possible to release the radiation filter from the housing only after the tilted radiation filter is displaced. In this manner a more user-friendly exchange of the radiation filter becomes possible and also any abrupt dropping of the radiation filter is avoided, since by means of such a swivelling mechanism the dropping of the radiation filter and thus its breakage can be effectively prevented.

It is advantageous if the at least one radiation filter is made rectangular, in which case its length and its width can range from 215 mm to 240 mm. Especially preferred is a radiation filter length of 230 mm and a radiation filter width of 225 mm. It has furthermore proven worth while if the at least one radiation filter is an interference filter, since with it the ultraviolet content can be controlled and the visible portion of the light can be suppressed.

It is best if at least one air intake opening is present between the at least one radiation filter and the housing. Of course it must be assured that no unfiltered portion of the radiation leaves the housing through the air intake opening. It has likewise been found to be good if at least one air intake opening is present in the housing between the at least one radiation filter and the reflector. Thus cooling air can flow through the air intake opening into the area between the radiation filter and the radiation emitting area of the reflector and be drawn from there through exhaust openings to the outside of the reflector.

It has proven to be especially beneficial if a first radiation filter is present and plane-parallel thereto a second radiation filter, the second radiation filter being arrayed between the radiation emitting area of the reflector and the first radiation filter, and the first radiation filter is an interference filter. The second radiation filter is in that case preferably in the form of an ultraviolet filter or infrared filter.

For safety against breakage of the at least one radiation filter, at least one touch contact is preferably disposed on the housing, which rests on the at least one radiation filter. In that case the touch contact can be carried through the reflector, perpendicular to the radiation emitting area of the reflector, or else it can be carried through the intake plate perpendicular to the radiation emitting area of the reflector. The touch contact, however, can also be arranged on the intake plate and rest on the at least one radiation filter. In the event of the breakage of the monitored radiation filter, the change in the position of the touch contact interrupts the power supply to the tanning radiator and the user is protected against an uncontrolled dose of radiation.

In the area of the opening of the reflector a base is provided for the mechanical and electrical hook-up of a tanning radiator.

Between the at least one radiation filter and the intake plate a cover plate can be associated which is arranged at a distance from the intake plate and which has a cut-out which in vertical projection onto the at least one radiation filter has the magnitude of the radiation emitting area of the reflector. This cover plate protects the eye of the user against any intake openings present in the intake plate for cooling air.

The FIGS. 1 to 4 are intended by way of example to explain the tanning module of the invention.

Figure 1:
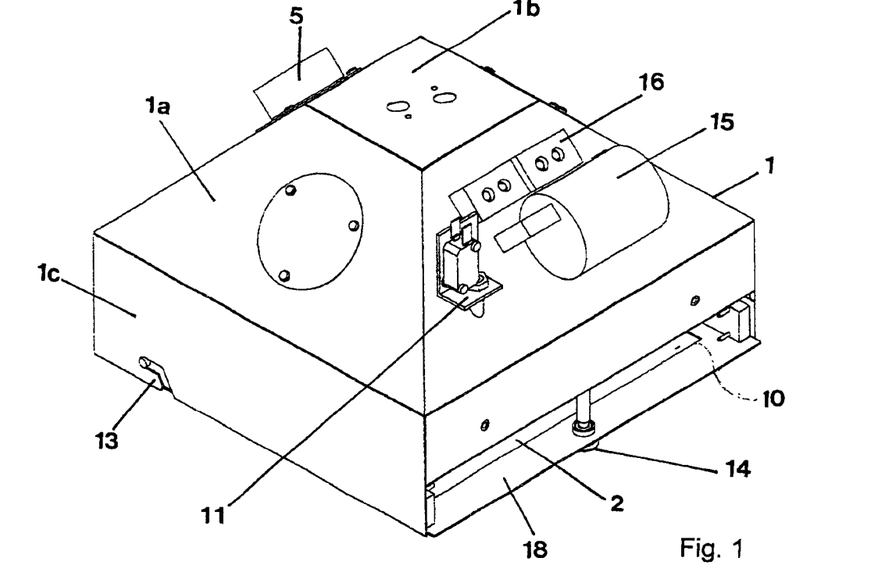
FIG. 1 shows the tanning module including radiation filter and electric connections in a three-dimensional view.

FIG. 1 shows a tanning module according to the invention including radiation filter and electric connections in a three-dimensional view. The housing 1 has on one side the shape of a four-sided pyramid 1a with rectangular base and flattened pyramid apex 1b. On three sloping sides of the pyramid are circular air exhaust openings, two of them closed, and one provided with a flange 5. The rectangular base is adjoined by a rectangular housing wall portion 1c. Into this is hooked, through opening 13, the radiation filter 2 (see FIG. 1b) which is within a frame structure, an air intake opening 10 remaining free. The frame structure for the radiation filter 2 contains among other things a frame 18 and the cover plate 17 (see FIG. 1b). The locking button 14 holds the radiation filter 2 in its position by means of a snap fastening mechanism which, upon opening, shuts off the tanning radiator. If the locking button is opened, the radiation filter 2 folds down with the frame structure, while the opening 13 prevents any complete drop-out. Not until the radiation filter 2 has been pulled forward is it completely releasable from the housing 1. On the side of the pyramid that has no air exhaust opening, a touch contact 11, starter 15 and electrical connections 16 are installed.

Figure 1A:
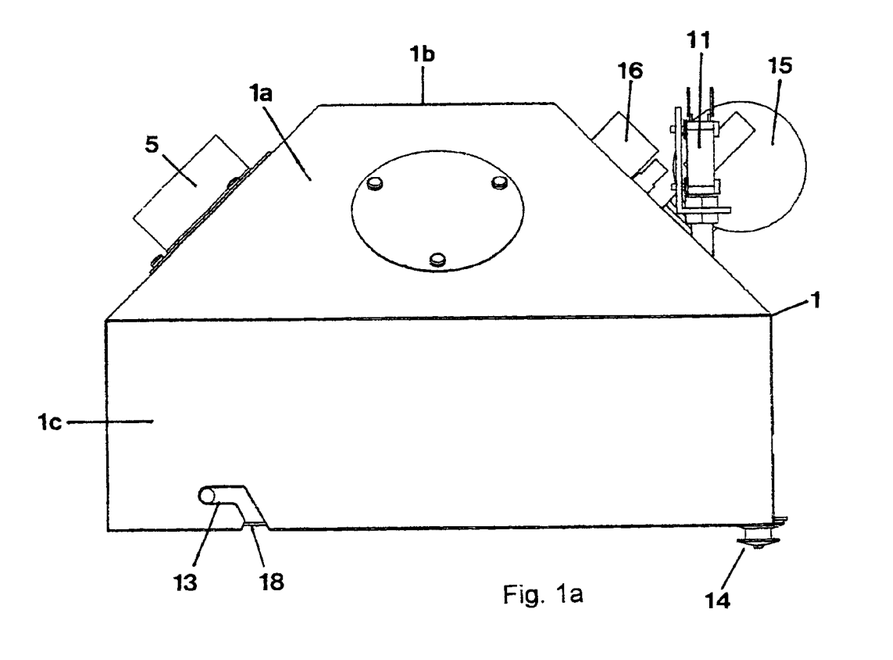
FIG. 1a shows the tanning module from FIG. 1 in a side view.

FIG. 1a shows the tanning module from FIG. 1 in a side view.

Figure 1B:
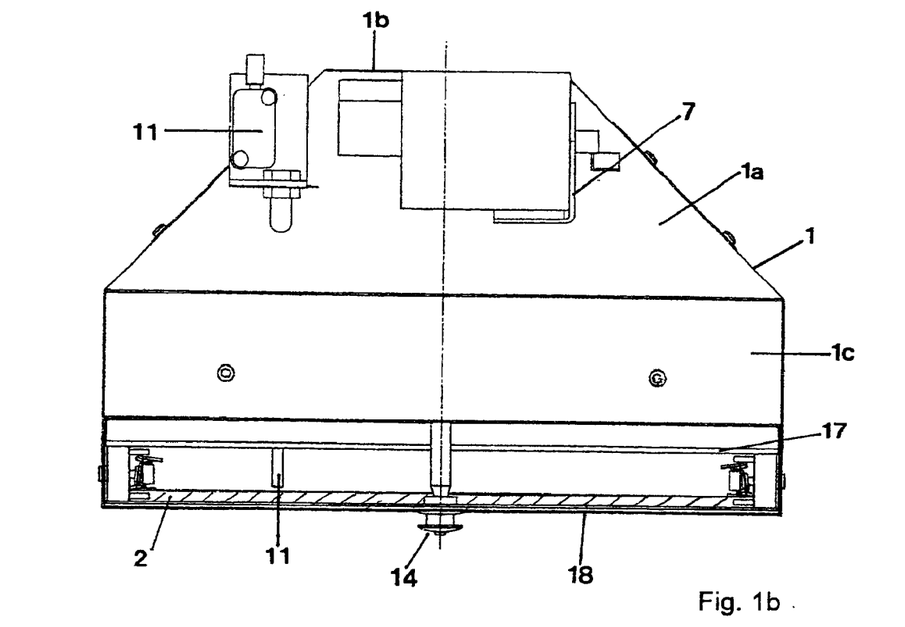
FIG. 1b shows the tanning module from FIG. 1 from the front.

FIG. 1b shows the front of the tanning module from FIG. 1, wherein the arrangement of the touch contact 11 on the radiation filter 2 can now be clearly seen. Moreover, a mounting 7 can be seen on which the starter 15 is installed.

Figure 1C:
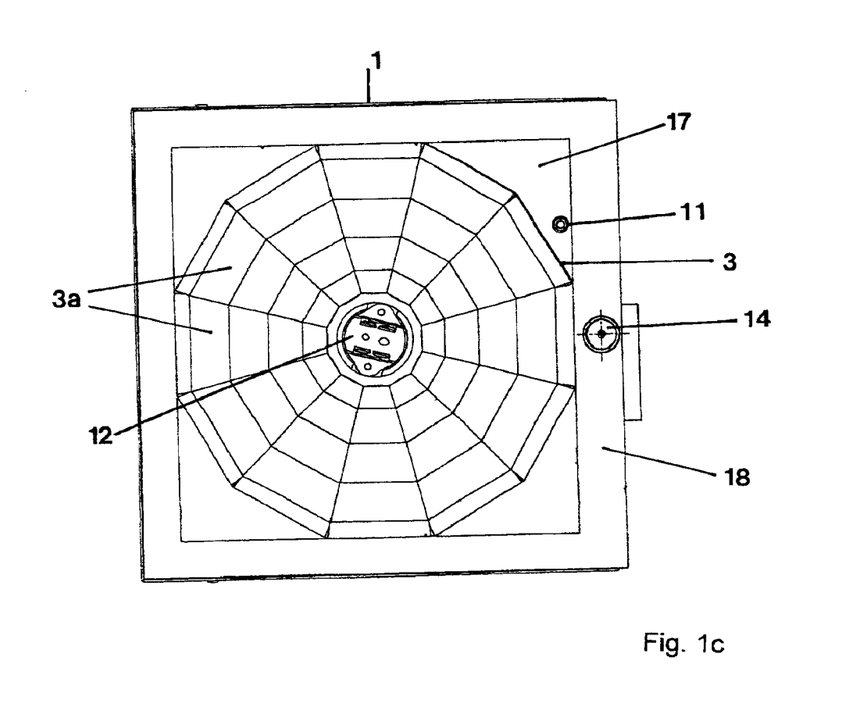
FIG. 1c shows the tanning module from FIG. 1 from below.

FIG. 1c shows the tanning module from FIG. 1 from below, the frame 18 and the cover plate 17 being visible. The transparent radiation filter 2 (see FIG. 1b) is between the frame 18 and the cover plate 17. A twelve-angled reflector 3 is present, which is formed of the facets 3a. The touch contact 11 is brought through the cover plate 17 and rests on the radiation filter 2 (see FIG. 1b). In the center of the reflector 3 the base 12 can be seen, including the electrical terminals for the tanning radiator.

Figure 1D:
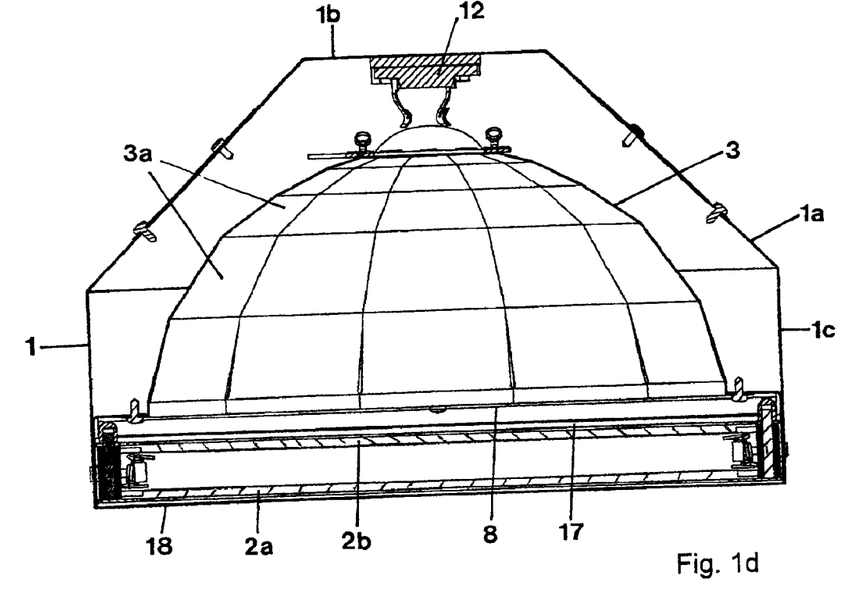
FIG. 1d shows the tanning module from FIG. 1b in section.

FIG. 1d shows the tanning module from FIG. 1b in section; here a first radiation filter 2a and a second radiation filter 2b are present. The reflector 3 is connected through an intake plate 8 to the housing 1.

Figure 1E:
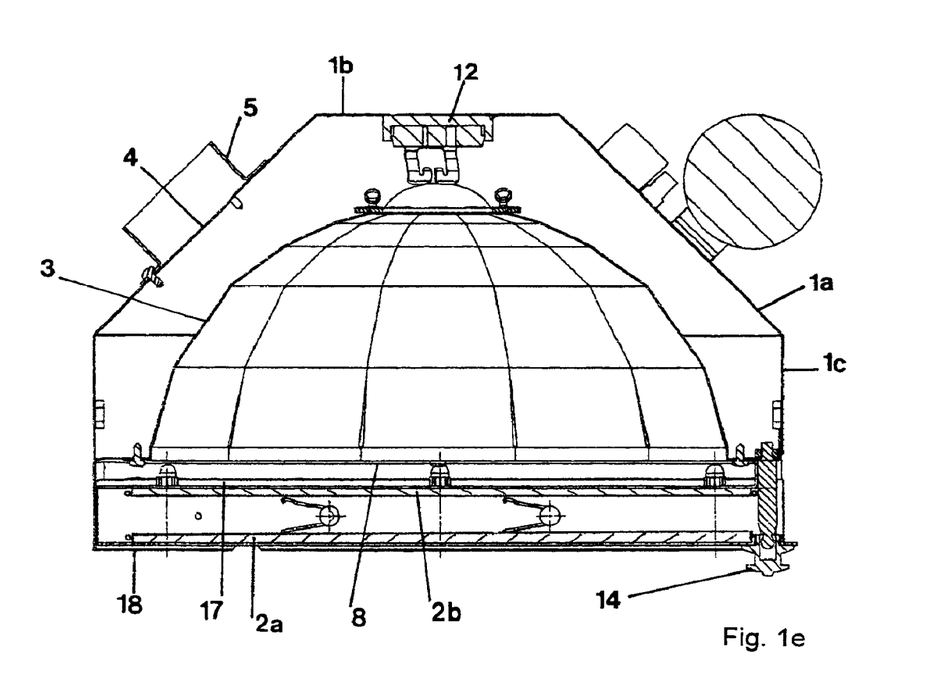
FIG. 1e shows the tanning module from FIG. 1a in section.

FIG. 1e shows the tanning module from FIG. 1a in section, where a first radiation filter 2a and a second radiation filter 2b are present. The air exhaust opening 4 on which the flange 5 is mounted can be seen. The reflector 3 is connected through the intake plate 8 to the housing 1.

Figure 2:
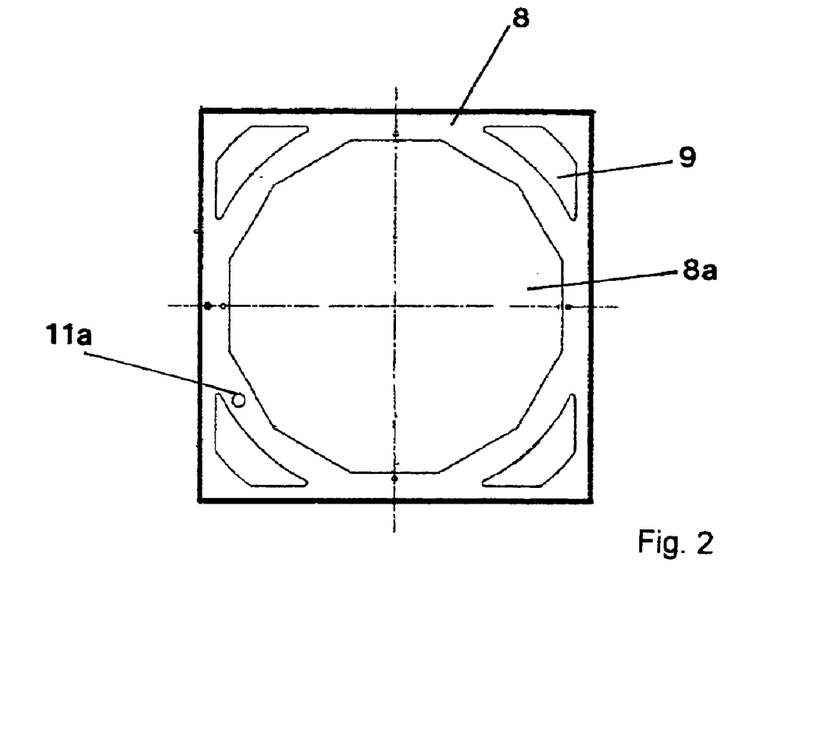
FIG. 2 shows an air intake plate including four intake openings.

FIG. 2 shows an intake plate 8 including a cut-out 8a for the reflector 3, as well as four trapezoidal intake openings 9. Moreover, an opening 11a is present for the touch contact 11 (see FIG. 1b).

Figure 2A:
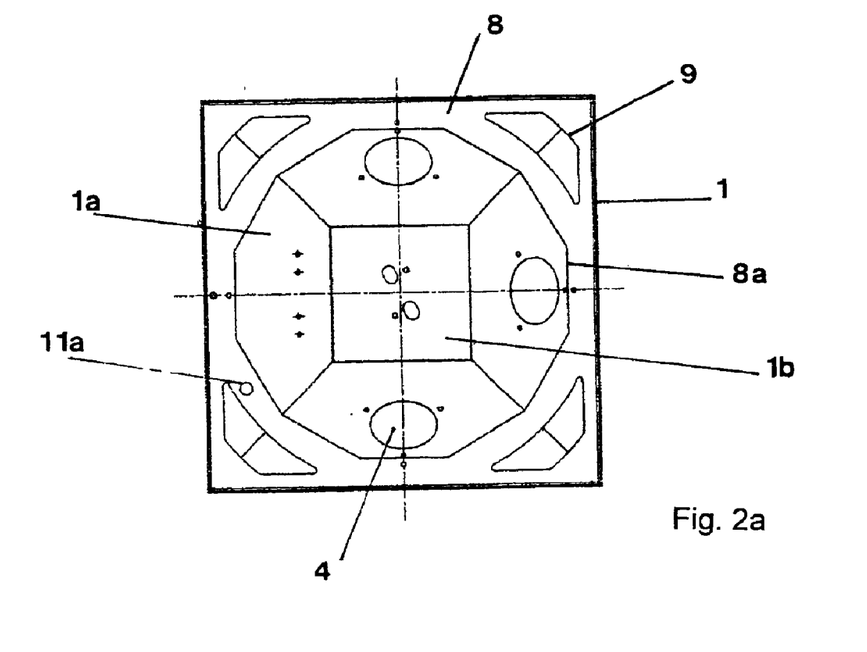
FIG. 2a shows the tanning module from FIG. 1 without radiation filter and reflector.

FIG. 2a shows the tanning module from FIG. 1c without the radiation filter 2 and reflector 3, wherein the view of the pyramid 1a and pyramid apex 1b is clear from the inside.

Figure 3:
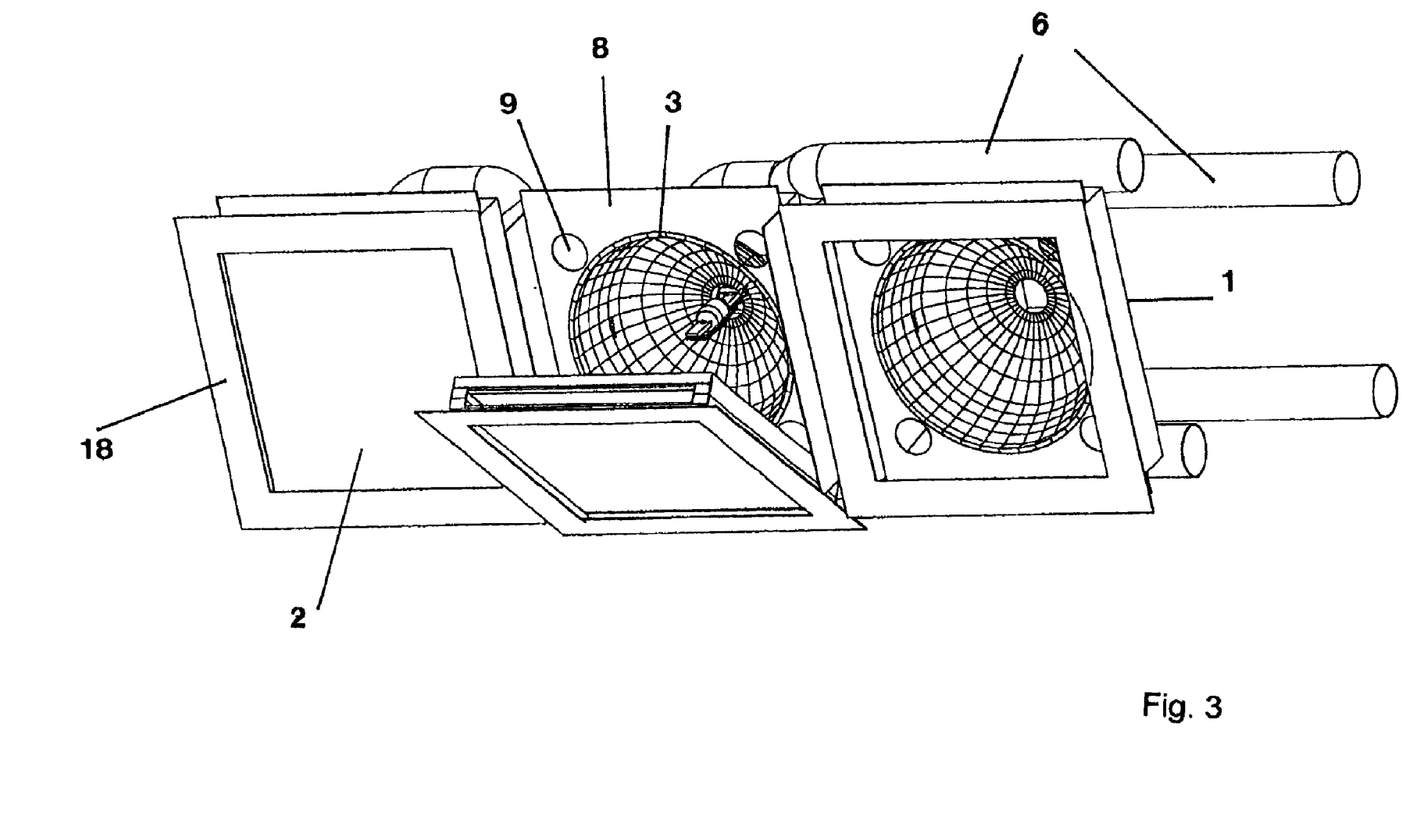
FIG. 3 shows a three-dimensional view of several tanning modules.

FIG. 3 shows a three-dimensional view of a plurality of tanning modules mounted one beside the other. On the left is a tanning module with radiation filter 2 and frame 18 in place. In the center is shown a tanning module with the radiation filter including the tanning radiator folded down, and the intake plate with circular intake openings 9 and the reflector 3 can be seen. On the right is shown a tanning module without radiation filter and without tanning radiator. All three modules are provided with air exhaust hoses 6.

Figure 4:
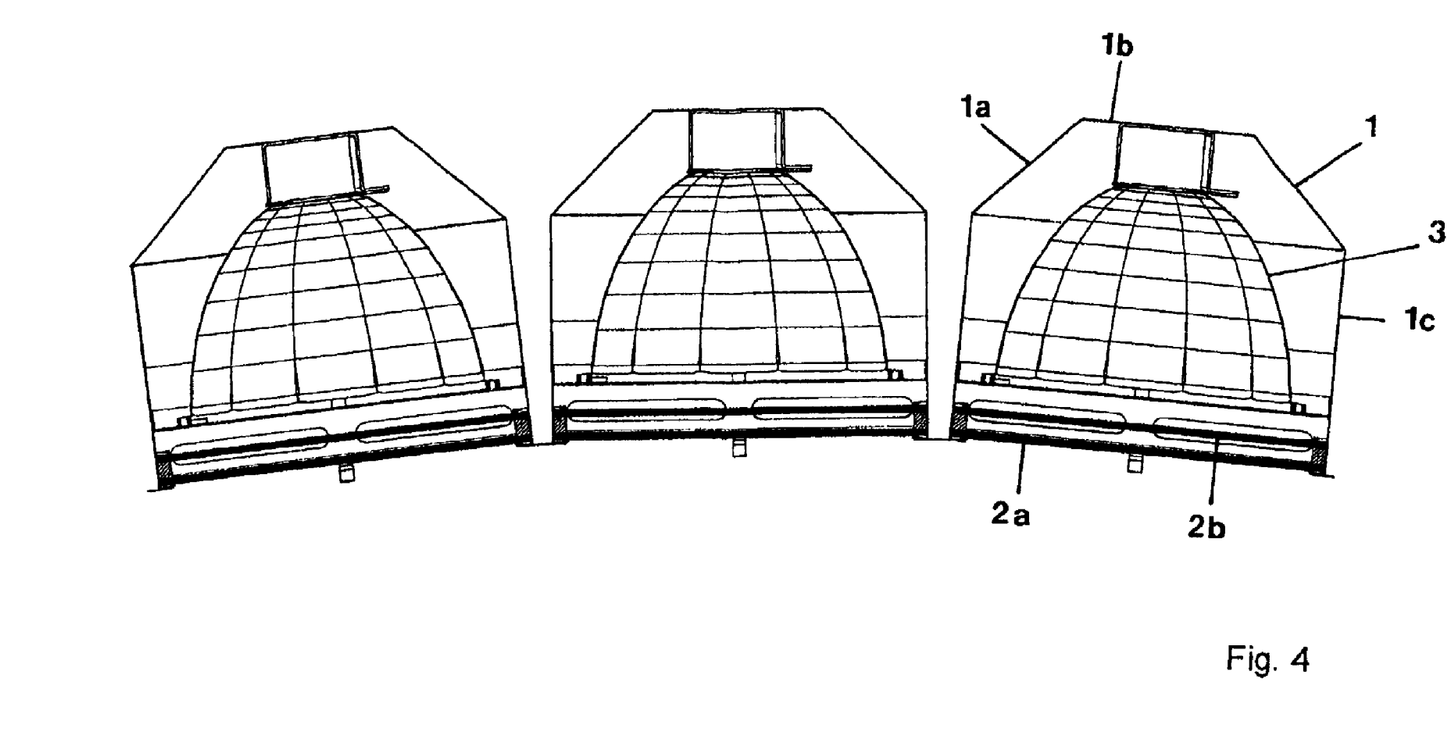
FIG. 4 shows three tanning modules, arranged as in FIG. 3, in section.

FIG. 4 shows three tanning modules in section which are arranged as in FIG. 3. A first radiation filter 2a and a second radiation filter 2b are present.

What is claimed is:

1. A tanning module comprising:
   a housing;
   a tridimensional reflector disposed in the housing; and
   at least one discoid radiation filter;
   wherein the at least one discoid radiation filter covers the radiation emitting area of the reflector and is disposed on a first side of the housing, at least one opening being provided in the reflector for the installation and electrical, connection of a tanning radiator, and the reflector having its maximum cross section in the plane of the radiation emitting area, wherein the housing is configured on a second side opposite the radiation filter in the form of a quadrilateral pyramid with a rectangular base and flattened pyramid apex and that the rectangular base faces in the direction of the at least one radiation filter, wherein an intake plate is disposed between housing and reflector in which case the radiation emitting area of the reflector is shifted upward or downward from the plane of the intake plate, at least one intake opening being formed between intake plate and reflector, and the intake plate has a cut-out for the reflector which in vertical protection onto the at least one discoid radiation filter has the size of the radiation emitting area of the reflector.

2. The tanning module according to claim 1, wherein the at least one discoid radiation filter is aligned parallel to the radiation emitting area of the reflector.

3. The tanning module according to claim 1, wherein the base of the pyramid is aligned parallel to the at least one discoid radiation filter.

4. The tanning module according to claim 1, wherein the flattened pyramid apex is formed by a planar part of the housing wall.

5. The tanning module according to claim 4, wherein the planar housing wall portion is aligned parallel to the base of the pyramid.

6. The tanning module according to claim 1, wherein the flattened pyramid apex is formed by a vaulted housing wall portion.

7. The tanning module according to claim 6, wherein the vaulted housing wall portion is configured concavely or convexly with respect to the base of the pyramid.

8. The tanning module according to claim 1, wherein a rectangular housing wall area adjoins the base of the pyramid.

9. The tanning module according to claim 1, wherein the reflector is cupular or tub-shaped.

10. The tanning module according to claim 9, wherein the bottom of the cupular or tub-shaped reflector is vaulted.

11. The tanning module according to claim 9, wherein the bottom of the capular or tub-shaped bottom of the reflector is made plane-parallel to the at least one discoid radiation filter.

12. The tanning module according to claim 1, wherein a perimeter of the reflector parallel to the radiation emitting area describes a circle, an ellipse, a rectangle or a polygon.

13. The tanning module according to claim 12, wherein the reflector is formed of facets and the perimeter of the reflector parallel to the radiation emitting area describes a dodecagon.

14. The tanning module according to claim 13, wherein the reflector has a height of 90 mm to 95 mm and the dodecagon has in the plane of the radiation emitting area a maximum diameter (corner to corner) in the range of 210 mm to 230 mm.

15. The tanning module according to claim 14, wherein the reflector has a height of 93.6 mm and the dodecagon has in the plane of the radiation emitting area a maximum diameter (corner to corner) of 210 mm.

16. The tanning module according to claim 13, wherein the reflector has a height ranging from 110 mm to 125 mm, and the dodecagon has in the plane of the radiation emitting area a maximum diameter (corner to corner) ranging from 170 mm to 200 mm.

17. The tanning module according to claim 16, wherein the reflector has a height of 118.7 mm and the dodecagon has in the plane of radiation emitting area a maximum diameter (corner to corner) of 184 mm.

18. The tanning module according to claim 13, wherein the reflector has a height ranging from, 75 mm to 90 mm, and The dodecagon has in the plane of the radiation emitting area a maximum diameter (corner to corner) ranging from 205 mm to 235 mm.

19. The tanning module according to claim 18, wherein the reflector has a height of 118.7 mm and the dodecagon has in the plane of radiation emitting area a maximum diameter (corner to corner) of 184 mm.

20. The tanning module according to claim 1, wherein the housing has at least one air exhaust opening in the area or the pyramid.

21. The tanning module according to claim 20, wherein a flange is provided at the at least one air exhaust opening.

22. The tanning module according to claim 21, wherein an air exhaust hose is connected to the flange.

23. The tanning module according to claim 20, wherein a reducing disk is present to reduce the size of the air exhaust opening.

24. The tanning module according to claim 20, wherein an air exhaust opening is arranged on each of three sides of the pyramid.

25. The tanning module according to claim 1, wherein at least one mounting is disposed externally on the housing for electrical connections or components.

26. The tanning module according to claim 1, wherein the at least one discoid radiation filter is of rectangular shape.

27. The tanning module according to claim 26, wherein the at least one discoid radiation filter has a length and a width ranging from 215 mm 240 mm.

28. The tanning module according to claim 27, wherein the at least one discoid radiation filter has a length of 230 mm and a width of 225 mm.

29. The tanning module according to claim 1, wherein at least one discoid radiation filter is an interference filter.

30. The tanning module according to claim 29, wherein a first discoid radiation filter is present, and plane-parallel thereto a second discoid radiation filter disposed between the radiation emitting area of the reflector and the first discoid radiation filter, wherein the first discoid radiation filter is an interference filter.

31. The tanning module according to claim 30, wherein the second discoid radiation filter is an ultraviolet filter or an infrared filter.

32. The tanning module according to claim 1, wherein at least one air intake opening is present between the at least one dicoid radiation filter and the housing.

33. The tanning module according to claim 1, wherein to protect the at least one discoid radiation filter against breakage at least one touch contact is disposed on the housing, which rests at the at least one radiation filter.

34. The tanning module according to claim 33, wherein the touch contact is guided through the reflector perpendicular to the radiation emitting area of the reflector.

35. The tanning module according to claim 33, wherein the touch contact is guided through the intake plate perpendicular to the radiation emitting area of the reflector.

36. The tanning module according to claim 1, wherein to indicate breaking of the at least one discoid radiation filter at least one touch contact is disposed on the intake plate and rests on the at least one discoid radiation filter.

37. The tanning module according to claim 1, wherein a base is provided in the area of the at least one opening in the reflector for the mechanical and electrical connection of the tanning radiator.

38. The tanning module according to claim 1, wherein between the at least one discoid radiation filter and the intake plate a cover plate is disposed, which is arranged at a distance from the intake plate and which has a cut-out which in vertical projection onto the at least one discoid radiation filter has the size of the radiation emitting area of the reflector.

39. The tanning module of claim 1, wherein the at least one radiation filter is releasable from the housing through a swivelling mechanism.

40. The tanning module according to claim 1, wherein the reflector is fastened to the housing only through the intake plate.

41. The tanning module according to claim 1 wherein at least one air intake opening is present in the housing between the at least one discoid radiation filter and the reflector.

42. A tanning module comprising:
   a housing:
   a tridimensional reflector disposed in the housing; and
   at least one discoid radiation filter;
   wherein the at least one discoid radiation filter covers the radiation emitting area of the reflector and is disposed on a first side of the housing, at least one opening being provided in the reflector for the installation and electrical connection of a tanning radiator, and the reflector having its maximum cross section in the plane of the radiation emitting area, characterized in that the housing is configured on a second side opposite the radiation filter in the form of a quadrilateral pyramid with a rectangular base and flattened pyramid apex and that the rectangular base faces in the direction of the at least one radiation filter,
   wherein an intake plate joins the housing and the reflector on all sides in the area of the radiation emitting area of the reflector, the intake plate having at least one intake opening and also has a cut-out for the reflector which in vertical projection onto the at least one discoid radiation filter has the size of the radiation emitting area of the reflector.

43. The tanning module according to claim 42, wherein the at least one discoid radiation filter is aligned parallel to the radiation emitting area of the reflector.

44. The tanning module according to claim 42, wherein the base of the pyramid is aligned parallel to the at least one discoid radiation filter.

45. The tanning module according to claim 42, wherein a rectangular housing wall area adjoins the base of the pyramid.

46. The tanning module according to claim 42, wherein at least one mounting is disposed externally on the housing for electrical connections or components.

47. The tanning module according to claim 42, wherein the at least one discoid radiation filter is releasable from the housing through a swivelling mechanism.

48. The tanning module according to claim 42, wherein at least one air intake opening is present in the housing between the at least one discoid radiation filter and the reflector.

49. The tanning module according to claim 42, wherein to indicate breaking of the at least one discoid radiation filter at least one touch contact is disposed on the intake plate and rests on the at least one discoid radiation filter.

50. The tanning module according to claim 42, wherein a base is provided in the area of the at least one opening in the reflector for the mechanical and electrical connection of the tanning radiator.

51. The tanning module according to claim 42, wherein at least one air intake opening is present between the at least one discoid radiation filter and the housing.

52. The tanning module according to claim 42, wherein the intake plate has a rectangular perimeter, that the perimeter of the reflector parallel to the radiation emitting area describes a circle, an ellipse or a polygon, and that the at least one intake opening is disposed in the area of a corner of the intake plate.

53. The tanning module according to claim 52, wherein four intake openings are formed in the intake plate and that one each of that four intake openings is disposed in another corner of the intake plate.

54. The tanning module according to claim 42, wherein at least one intake opening is enlarged along the sides of the intake plate.

55. The tanning module according to claim 54, wherein the intake opening is trapezoidal, the long side of the trapeze facing toward the reflector.

56. The tanning module according to claim 55, wherein the long side of the trapeze as well as its opposite side are curved.

57. The tanning module according to claim 42, wherein the flattened pyramid apex is formed by a planar part of the housing wall.

58. The tanning module according to claim 57, wherein the planar housing wall portion is aligned parallel to the base of the pyramid.

59. The tanning module according to claim 42, wherein the flattened pyramid apex is formed by a vaulted housing wall portion.

60. The tanning module according to claim 59, wherein the vaulted housing wall portion is configured concavely or convexly with respect to the base of the pyramid.

61. The tanning module according to claim 42, wherein the reflector is cupular or tub-shaped.

62. The tanning module according to claim 61, wherein the bottom of the capular or tub-shaped reflector is vaulted.

63. The tanning module according to claim 61, wherein the bottom, of the capular or tub-shaped bottom of the reflector is made plane-parallel to the at least one discoid radiation filter.

64. The tanning module according to claim 42, wherein the at least one discoid radiation filter is of rectangular shape.

65. The tanning module according to claim 64, wherein the at least one discoid radiation filter has a length and a width ranging from 215 mm to 240 mm.

66. The tanning module according to claim 65, wherein the at least one discoid radiation filter has a length of 230 mm and a width of 225 mm.

67. The tanning module according to claim 42, wherein the at least one discoid radiation filter is an interference filter.

68. The tanning module according to claim 67, wherein a first discoid radiation filter is present, and plane-parallel thereto a second discoid radiation filter disposed between the radiation emitting area of the reflector and the first discoid radiation filter, wherein the first discoid radiation filter is an interference filter.

69. The tanning module according to claim 68, wherein the second discoid radiation filter is an ultraviolet filter or an infrared filter.

70. The tanning module according to claim 42, wherein to protect the at least one discoid radiation filter against breakage at least one touch contact is disposed on the housing, which rests at the at least one radiation filter.

71. The tanning module according to claim 70, wherein the touch contact is guided through the reflector perpendicular to the radiation emitting area of the reflector.

72. The tanning module according to claim 70, wherein the touch contact is guided through the intake plate perpendicular to the radiation emitting area of the reflector.

73. The tanning module according to claim 42, wherein a perimeter of the reflector parallel to the radiation emitting area describes a circle, an ellipse, a rectangle or a polygon.

74. The tanning module according to claim 73, wherein the reflector is formed of facets and the perimeter of the reflector parallel to the radiation emitting area describes a dodecagon.

75. The tanning module according to claim 74, wherein the reflector has a height of 90 mm to 95 mm and the dodecagon has in the plane of the radiation emitting area a maximum diameter (corner to corner) in the range of 210 mm to 230 mm.

76. The tanning module according to claim 75, wherein the reflector has a height of 93.6 mm and the dodecagon has in the plane of the radiation emitting area a maximum diameter (corner to corner) of 210 mm.

77. The tanning module according to claim 74, wherein the reflector has a height ranging from 110 mm to 125 mm, and the dodecagon has in the plane of the radiation emitting area a maximum diameter (corner to corner) ranging from 170 mm to 200 mm.

78. The tanning module according to claim 77, wherein the reflector has a height of 118.7 mm and the dodecagon has in the plane of radiation emitting area a maximum diameter (corner to corner) of 184 mm.

79. The tanning module according to claim 74, wherein the reflector has a height ranging from 75 mm to 90 mm, and the dodecagon has in the plane of the radiation emitting area a maximum diameter (corner to corner) ranging from 205 mm to 235 mm.

80. The tanning module according to claim 79, wherein the reflector has a height of 118.7 mm and the dodecagon has in the plane of radiation emitting area a maximum diameter (corner to corner) of 184 mm.

81. The tanning module according to claim 42, wherein the housing has at least one air exhaust opening in the area of the pyramid.

82. The tanning module according to claim 81, wherein a reducing disk is present to reduce the size of the air exhaust opening.

83. The tanning module according to claim 81, wherein an air exhaust opening is arranged on each of three sides of the pyramid.

84. The tanning module according to claim 81, wherein a flange is provided at the at least one air exhaust opening.

85. The tanning module according to claim 84, wherein an air exhaust hose is connected to the flange.

* * * * *